United States Patent

Brydon et al.

Patent Number: 6,155,986
Date of Patent: Dec. 5, 2000

[54] MONITORING OF ORO-NASAL RESPIRATION

[75] Inventors: John William Ernest Brydon, Waverton, Australia; Patrick Michael Piccione, Cambridge, Mass.

[73] Assignee: ResMed Limited, North Ryde, Australia

[21] Appl. No.: 08/894,092

[22] PCT Filed: Jun. 7, 1996

[86] PCT No.: PCT/AU96/00347

§ 371 Date: Jul. 21, 1998

§ 102(e) Date: Jul. 21, 1998

[87] PCT Pub. No.: WO96/41571

PCT Pub. Date: Dec. 27, 1996

[30] Foreign Application Priority Data

Jun. 8, 1995 [AU] Australia ................... PN3441

[51] Int. Cl.[7] ........................................... A61B 5/08
[52] U.S. Cl. .................. 600/538; 600/533; 600/529; 128/911
[58] Field of Search ................ 600/538, 532, 600/533, 537, 529, 531; 73/23.3; 128/200.24, 911

[56] References Cited

U.S. PATENT DOCUMENTS

| | | |
|---|---|---|
| Re. 35,295 | 7/1996 | Estes et al. . |
| Re. 35,339 | 10/1996 | Rapoport . |
| 2,904,033 | 9/1959 | Shane . |
| 3,502,100 | 3/1970 | Jonson . |
| 3,559,638 | 2/1971 | Potter . |
| 3,595,228 | 7/1971 | Simon et al. . |
| 3,611,801 | 10/1971 | Paine et al. . |
| 3,726,270 | 4/1973 | Griffis et al. ............ 600/532 |
| 3,741,208 | 6/1973 | Jonsson et al. . |
| 3,802,417 | 4/1974 | Lang . |
| 3,932,054 | 1/1976 | McKelvey . |

(List continued on next page.)

FOREIGN PATENT DOCUMENTS

| | | |
|---|---|---|
| 62221/90 | 3/1991 | Australia . |
| 33877/93 | 4/1993 | Australia . |
| 38508/93 | 7/1993 | Australia . |
| 48748/93 | 9/1993 | Australia . |
| 52628/93 | 12/1993 | Australia . |
| 34471/95 | 2/1996 | Australia . |
| 40711-95 | 4/1996 | Australia . |
| 0 066 451 A1 | 12/1982 | European Pat. Off. . |
| 164-500 | 3/1985 | European Pat. Off. . |
| 0 171 321 A1 | 2/1986 | European Pat. Off. . |
| 0 425 092 A1 | 9/1989 | European Pat. Off. . |
| 0 452 001 A2 | 3/1990 | European Pat. Off. . |
| 0 461 281 A1 | 12/1991 | European Pat. Off. . |
| 0 656 216 A2 | 6/1995 | European Pat. Off. . |
| 0 661 071 A1 | 7/1995 | European Pat. Off. . |
| 0 709 107 A1 | 5/1996 | European Pat. Off. . |
| 0 714 670 A2 | 6/1996 | European Pat. Off. . |
| 0 765 631 A2 | 4/1997 | European Pat. Off. . |
| 0 788 805 A2 | 8/1997 | European Pat. Off. . |
| 2682042-A1 | 4/1993 | France . |
| 3345067 A1 | 6/1984 | Germany . |

(List continued on next page.)

*Primary Examiner*—Cary O'Connor
*Assistant Examiner*—Navin Natnithithadha
*Attorney, Agent, or Firm*—Pillsbury Madison & Sutro LLP

[57] ABSTRACT

Apparatus for monitoring oro-nasal respiration. A pair of nasal prongs, suitable for insertion into the lower portion of the nares, join together via a small plenum chamber to form a single tube conveying the nasal pressure towards an electrical pressure transducer. Another prong is held in proximity with the patient's mouth. A baffle element extends downwards from a location above the open end of the prong to redirect a portion of oral airflow. The oral tube extends towards the electrical pressure transducers and conjoins with the nasal tube at a junction to form a common tube connected to the pressure transducer. The relative lengths and/or diameters of the nasal tube and the oral tube are arranged so that the respective pneumatic impedances are different, so that the contributions of respiratory airflow from each of said tubes are substantially equal.

36 Claims, 9 Drawing Sheets

U.S. PATENT DOCUMENTS

| | | |
|---|---|---|
| 3,989,037 | 11/1976 | Franetzki . |
| 4,006,634 | 2/1977 | Billette et al. . |
| 4,083,245 | 4/1978 | Osborn . |
| 4,119,096 | 10/1978 | Drews . |
| 4,206,754 | 6/1980 | Cox et al. . |
| 4,312,235 | 1/1982 | Daigle . |
| 4,322,594 | 3/1982 | Brisson . |
| 4,381,788 | 5/1983 | Douglas . |
| 4,433,693 | 2/1984 | Hochstein . |
| 4,481,944 | 11/1984 | Bunnell . |
| 4,519,399 | 5/1985 | Hori ........................................ 600/537 |
| 4,550,615 | 11/1985 | Grant . |
| 4,550,726 | 11/1985 | McEwen . |
| 4,570,631 | 2/1986 | Durkan . |
| 4,580,575 | 4/1986 | Birnbaum et al. . |
| 4,592,880 | 6/1986 | Murakami . |
| 4,595,016 | 6/1986 | Fertig et al. . |
| 4,602,644 | 7/1986 | DiBenedetto et al. . |
| 4,648,396 | 3/1987 | Raemer . |
| 4,655,213 | 4/1987 | Rapoport et al. . |
| 4,686,974 | 8/1987 | Sato et al. . |
| 4,738,266 | 4/1988 | Thatcher . |
| 4,747,403 | 5/1988 | Gluck et al. . |
| 4,773,411 | 9/1988 | Downs . |
| 4,777,963 | 10/1988 | McKenna . |
| 4,802,485 | 2/1989 | Bowers et al. . |
| 4,838,258 | 6/1989 | Dryden et al. . |
| 4,844,085 | 7/1989 | Gattinoni . |
| 4,913,401 | 4/1990 | Handke . |
| 4,928,684 | 5/1990 | Breitenfelder et al. . |
| 4,938,212 | 7/1990 | Snook et al. . |
| 4,944,310 | 7/1990 | Sullivan . |
| 4,957,107 | 9/1990 | Sipin . |
| 4,960,118 | 10/1990 | Pennock . |
| 4,971,065 | 11/1990 | Pearce . |
| 4,982,738 | 1/1991 | Griebel . |
| 4,989,599 | 2/1991 | Carter . |
| 5,009,635 | 4/1991 | Scarberry . |
| 5,024,219 | 6/1991 | Dietz . |
| 5,046,491 | 9/1991 | Derrick ........................ 128/200.24 |
| 5,048,515 | 9/1991 | Sanso . |
| 5,052,400 | 10/1991 | Dietz . |
| 5,063,938 | 11/1991 | Beck et al. ..................... 600/537 |
| 5,065,756 | 11/1991 | Rapoport . |
| 5,069,222 | 12/1991 | McDonald, Jr. . |
| 5,090,248 | 2/1992 | Cimmino et al. . |
| 5,099,837 | 3/1992 | Russel, Sr. et al. . |
| 5,107,830 | 4/1992 | Younes . |
| 5,107,831 | 4/1992 | Halpern et al. . |
| 5,117,819 | 6/1992 | Servidio et al. . |
| 5,129,390 | 7/1992 | Chopin et al. . |
| 5,134,995 | 8/1992 | Gruenke et al. . |
| 5,148,802 | 9/1992 | Sanders et al. . |
| 5,161,525 | 11/1992 | Kimm et al. . |
| 5,161,541 | 11/1992 | Bowman et al. . |
| 5,165,398 | 11/1992 | Bird . |
| 5,170,798 | 12/1992 | Riker . |
| 5,190,048 | 3/1993 | Wilkinson . |
| 5,195,528 | 3/1993 | Hok . |
| 5,199,424 | 4/1993 | Sullivan et al. . |
| 5,203,343 | 4/1993 | Axe et al. . |
| 5,231,979 | 8/1993 | Rose et al. . |
| 5,239,994 | 8/1993 | Atkins . |
| 5,239,995 | 8/1993 | Estes et al. . |
| 5,245,995 | 9/1993 | Sullivan et al. . |
| 5,259,373 | 11/1993 | Gruenk et al. . |
| 5,271,391 | 12/1993 | Graves . |
| 5,303,698 | 4/1994 | Tobia et al. . |
| 5,303,700 | 4/1994 | Weismann et al. . |
| 5,311,875 | 5/1994 | Stasz . |
| 5,313,937 | 5/1994 | Zdrojkowski . |
| 5,335,656 | 8/1994 | Bowe et al. . |
| 5,343,878 | 9/1994 | Scarberry et al. . |
| 5,353,788 | 10/1994 | Miles . |
| 5,360,008 | 11/1994 | Campbell, Jr. . |
| 5,373,842 | 12/1994 | Olsson et al. . |
| 5,394,882 | 3/1995 | Mawhinney . |
| 5,400,777 | 3/1995 | Olsson et al. . |
| 5,433,193 | 7/1995 | Sanders et al. . |
| 5,443,061 | 8/1995 | Champain et al. . |
| 5,458,137 | 10/1995 | Axe et al. . |
| 5,479,939 | 1/1996 | Ogino . |
| 5,483,969 | 1/1996 | Testerman et al. . |
| 5,490,502 | 2/1996 | Rapoport et al. . |
| 5,492,113 | 2/1996 | Estes et al. . |
| 5,503,146 | 4/1996 | Froehlich et al. . |
| 5,507,282 | 4/1996 | Younes . |
| 5,509,414 | 4/1996 | Hok ........................................ 600/438 |
| 5,513,631 | 5/1996 | McWilliams . |
| 5,517,983 | 5/1996 | Deighan et al. . |
| 5,522,382 | 6/1996 | Sullivan et al. . |
| 5,535,738 | 7/1996 | Estes et al. . |
| 5,535,739 | 7/1996 | Rapoport et al. . |
| 5,537,997 | 7/1996 | Mechlenburg et al. . |
| 5,540,219 | 7/1996 | Mechlenburg et al. . |
| 5,540,733 | 7/1996 | Testerman et al. . |
| 5,546,933 | 8/1996 | Rapoport et al. . |
| 5,546,952 | 8/1996 | Erickson . |
| 5,549,655 | 8/1996 | Erickson . |
| 5,551,418 | 9/1996 | Estes et al. . |
| 5,551,419 | 9/1996 | Froehlich et al. . |
| 5,558,099 | 9/1996 | Bowman et al. . |
| 5,588,439 | 12/1996 | Hollub . |
| 5,598,838 | 2/1997 | Servidio et al. . |
| 5,605,151 | 2/1997 | Lynn . |
| 5,632,269 | 5/1997 | Zdrojkowski . |
| 5,633,552 | 5/1997 | Lee et al. . |
| 5,645,054 | 7/1997 | Cotner et al. . |
| 5,655,522 | 8/1997 | Mechlenburg et al. . |

FOREIGN PATENT DOCUMENTS

| | | |
|---|---|---|
| 296 12 119 U1 | 12/1996 | Germany . |
| 195 36 631 A1 | 3/1997 | Germany . |
| 4-70516 | 3/1992 | Japan . |
| 06249741 | 9/1994 | Japan . |
| 6-249742 | 9/1994 | Japan . |
| 8019610 | 1/1996 | Japan . |
| 467041-B | 5/1992 | Sweden . |
| 2 147 506 | 5/1985 | United Kingdom . |
| 2 166 871 | 5/1986 | United Kingdom . |
| 2 221 302 | 1/1990 | United Kingdom . |
| 2 294 400 | 5/1996 | United Kingdom . |
| WO 82-03548 | 10/1982 | WIPO . |
| WO 86/05965 | 10/1986 | WIPO . |
| WO 87/02577 | 5/1987 | WIPO . |
| WO 88/10108 | 12/1988 | WIPO . |
| WO 90/14121 | 11/1990 | WIPO . |
| WO 91/12051 | 8/1991 | WIPO . |
| WO 92/11054 | 7/1992 | WIPO . |
| WO 92/22244 | 12/1992 | WIPO . |
| WO 93/08857 | 5/1993 | WIPO . |
| WO 93/09834 | 5/1993 | WIPO . |
| WO 93/21982 | 11/1993 | WIPO . |
| WO 93/24169 | 12/1993 | WIPO . |
| WO 94/04071 | 3/1994 | WIPO . |
| WO 94/20018 | 9/1994 | WIPO . |
| WO 94/23780 | 10/1994 | WIPO . |
| WO 95/32016 | 11/1995 | WIPO . |
| WO 96/32055 | 10/1996 | WIPO . |

| | | | | | |
|---|---|---|---|---|---|
| WO 96/36279 | 11/1996 | WIPO . | WO 97/10868 | 3/1997 | WIPO . |
| WO 96/40337 | 12/1996 | WIPO . | WO 97/14354 | 4/1997 | WIPO . |
| WO 96/41571 | 12/1996 | WIPO . | WO 97/15343 | 5/1997 | WIPO . |
| WO 97/02064 | 1/1997 | WIPO . | WO 97/18752 | 5/1997 | WIPO . |
| WO 97/05824 | 2/1997 | WIPO . | WO 97/20499 | 6/1997 | WIPO . |
| WO 97/10019 | 3/1997 | WIPO . | WO 97/22377 | 6/1997 | WIPO . |

MONITORING OF ORO-NASAL RESPIRATION

FIELD OF THE INVENTION

This invention relates to apparatus and methods for monitoring oro-nasal respiration.

BACKGROUND OF THE INVENTION

In the medical study of respiration, including monitoring during sleep, it often is important to detect and classify respiration using the least invasive method possible. To this end the measurement of airflow in the proximity of the nose and mouth (i.e. oro-nasally) is an established technique. Although the majority of people breath through their nose while asleep it is important also to monitor oral airflow. The failure also to monitor oral airflow may lead to misinterpretation of mouth breathing as a cessation (apnea) or reduction (hypopnea) in respiration.

One of two methods of measurement are conventionally used to monitor oro-nasal airflow. The first is based on the location of a thermistor (or thermistors) in the oral and nasal airflows, as shown in FIG. 1. The thermistors 1 are connected to electronic circuitry 2 which measures their electrical resistance and outputs a signal 3 indicative of this resistance and/or a change therein. Airflow past the thermistor is measured by the increase in temperature of the exhaled air relative to ambient, as shown in FIG. 2, or alternatively by the cooling effect of a moving airflow past a thermistor which is warmed above ambient by an electrical current passing through it.

While this method of measurement is convenient and cheap, the low frequency cut-off point of the filtering circuitry necessary to remove noise from the flow signal to make it useable also removes higher frequency elements indicative of snoring or respiratory flow limitation. The phase response of such filtering also may distort the timing of respiration.

A second known method of measuring oro-nasal airflow, shown in FIG. 3, uses the well known pitot tube or Bernoulli effect, whereby a pressure which varies with flow rate is generated in a tube 4 by placing its open end parallel with, or at some intermediate angle to, the flow. The other end of the tube terminates at an electrical pressure transducer 5, the output signal 6 of which thus varies with flow rate.

Unlike the thermistor technique, the flow measurements derived from the pressure transducers 5 have a bandwidth adequate for detecting both snoring and flow limitation. FIG. 4 shows a typical pressure signal illustrating both instances. Such systems are routinely used for the detection of nasal respiration, but their use in measuring oral respiration is problematic due to the lower flow velocities often found in the wider oral cross-section compared to the narrower nasal passageway.

When the pressure transducer prior art method is used to measure both nasal and oral airflow, normally only one pressure transducer is fed by two sources. Two tubes 7 are located at the periphery of or just inside, the nares, and another single (or double) tube 8 is located in the vicinity of the lips, as shown in FIG. 5. These tubes join downstream into a common tube 9 in communication with the circuitry 5.

Oral flow measured in this way gives a significantly lower output (typically a factor of 6) from the pressure transducer than nasal flow. Additionally, the oro-nasal tube configuration further attenuates the oral flow by a factor of about two because for zero nasal flow there is a pressure drop down the tubing path from the oral inlet 8 to the nasal inlets 7, as exemplified in FIG. 6. This pneumatic "potential divider" effect is present in all configurations where two tube inlets join together via similar tubes.

The sensitivity of the oral channel also is highly dependent on the positioning of the oral tube 8. As shown in FIGS. 7a and 7b, if the tube end 10 is located in the centre of the airflow for exhalation with slightly opened lips 11 it will become insensitive if the mouth is opened further and the airflow profile changes.

SUMMARY OF THE INVENTION

The present invention is directed to overcoming or at least ameliorating one or more of the problems associated with the prior art pressure transducer technique. In one embodiment, the monitoring of oro-nasal respiration by separate oral and nasal tubes is arranged so that the signal due to nose breathing and due to mouth breathing are of the same amplitude at the point of measurement for any given flow rate.

Therefore, the invention discloses apparatus for monitoring oro-nasal respiration comprising a nasal tube for receiving nasal respiratory flow and an oral tube for receiving oral respiratory flow, the pneumatic impedances of the nasal tube and the oral tube being arranged to be different so that the contributions of respiratory airflow from each said tubes are substantially equal, and electrical transducer means to which both said oral tube and said nasal tube are coupled for generating an output signal representative of oro-nasal respiration.

The invention further discloses apparatus for detecting oro-nasal respiratory flow, comprising a nasal tube for receiving nasal respiratory flow and an oral tube for receiving oral respiratory flow, the pneumatic impedances of the nasal tube and the oral tube being arranged to be different so that the contributions of respiratory airflow from each said tube are substantially equal.

Preferably, the respective pneumatic impedances are in a ratio substantially the same as the ratio of amplitudes of nasal respiration flow and oral respiration flow.

Conveniently, the pneumatic impedances are arranged to be different by adjustment of the relative length of the nasal tube and the oral tube. In one form the nasal tube can be longer than the oral tube. The ratio of the nasal tube length to the oral tube length can be less than 5:1. Alternatively, the relative diameters of the nasal tube and the oral tube can be adjusted. The nasal tube can be of smaller diameter than, but the same length as, the oral tube. The reduced nasal tube diameter can be approximately $\frac{2}{3}$ of the oral tube. Furthermore, the relative length and the relative diameters both can be adjusted.

Preferably, the nasal tube terminates in two nasal prongs each arranged to be at the entrance of, or inserted into, the nares. The oral tube can terminate in an open ending to be arranged proximate the mouth. The oral tube can comprise two branched ends or two separate tubes.

In a preferred form at least the nasal prongs are contained within a nose mask for sealingly engaging the face in the region around the nose.

Preferably, said nasal tube and said oral tube conjoin into a common tube, the common tube being for connection with electrical transducer means. The transducer can be a pressure transducer or an airflow transducer.

Alternatively, the nasal tube and the oral tube can be separately connected with electrical transducer means.

Advantageously, the apparatus further comprises baffle means for location proximate a patient's mouth, and wherein the open end of said oral tube is interposed between said baffle means and the patient's mouth.

Preferably, said baffle element is shaped to generally direct oral respiratory flow to said open end of said oral tube. Yet further preferably, said baffle element is shaped to substantially cover the patient's mouth when at its fullest open extent.

Preferably, the output signal of the pressure transducer is a representation of respiratory flow, and the signal is applied to circuit means to derive output signals indicative of respiratory swing and snoring.

The invention further discloses a method for monitoring oro-nasal respiration comprising the steps of locating a nasal tube in the vicinity of a patient's nares to receive nasal respiratory flow, locating a mouth tube in the vicinity of the patient's mouth to receive mouth respiratory flow, arranging the pneumatic impedances of the nasal tube and the oral tube to be different so that the contributions of respiratory airflow from each said tube are substantially equal, and converting, by electrical transducer means, flow in said oral tube and said nasal tube to a signal representative of oro-nasal respiration.

Embodiments of the present invention advantageously offer improvements over the prior art by reducing the attenuation of the oral signal when it is conducted to a single pressure transducer in common with a nasal signal. Further, the embodiments reduce the relative disparity in amplitude between the oral and nasal signals, thereby allowing more consistent and continuous monitoring of oro-nasal respiration. Yet further, the positional dependence of the oral probe is reduced, thereby increasing the reproducability of measurement of the oral airflow for different degrees of mouth opening.

BRIEF DESCRIPTION OF THE DRAWINGS

Embodiments of the invention now will be described with reference to the accompanying drawings, in which.

DESCRIPTION OF PREFERRED EMBODIMENTS AND BEST MODE

Figure 1:
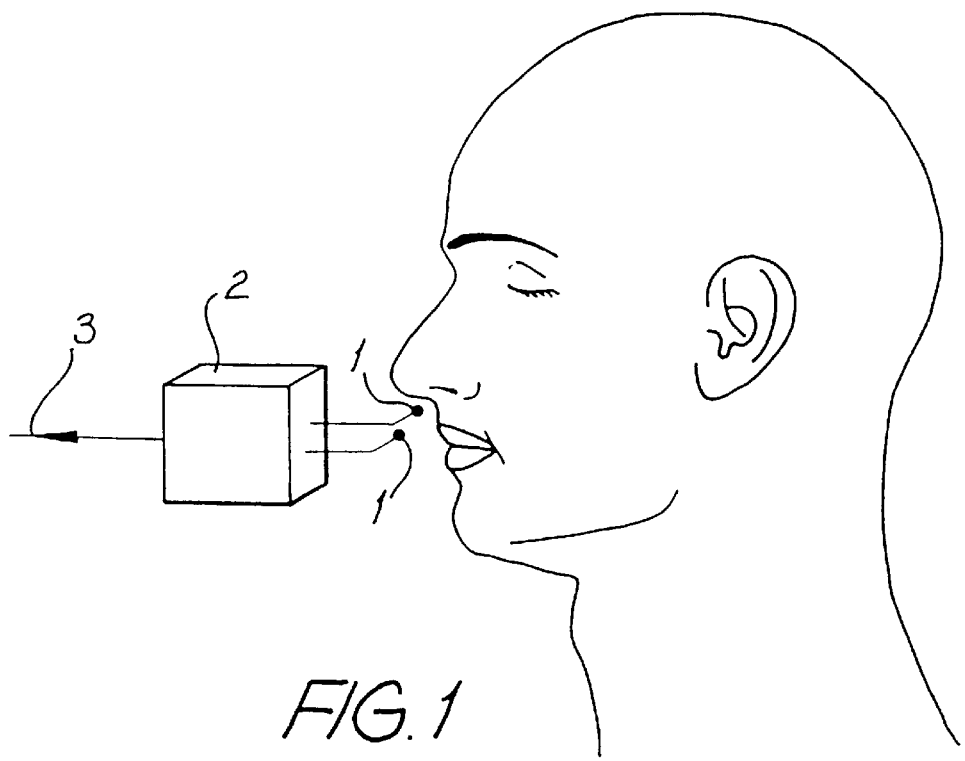
FIGS. 1 to 7 are prior art arrangements as already discussed.
Figure 2:
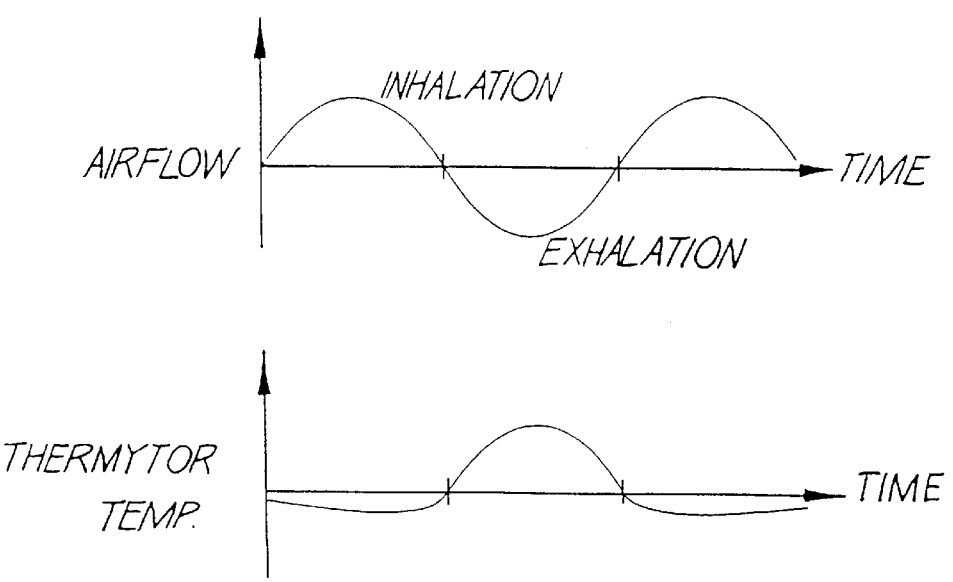
Figure 3:
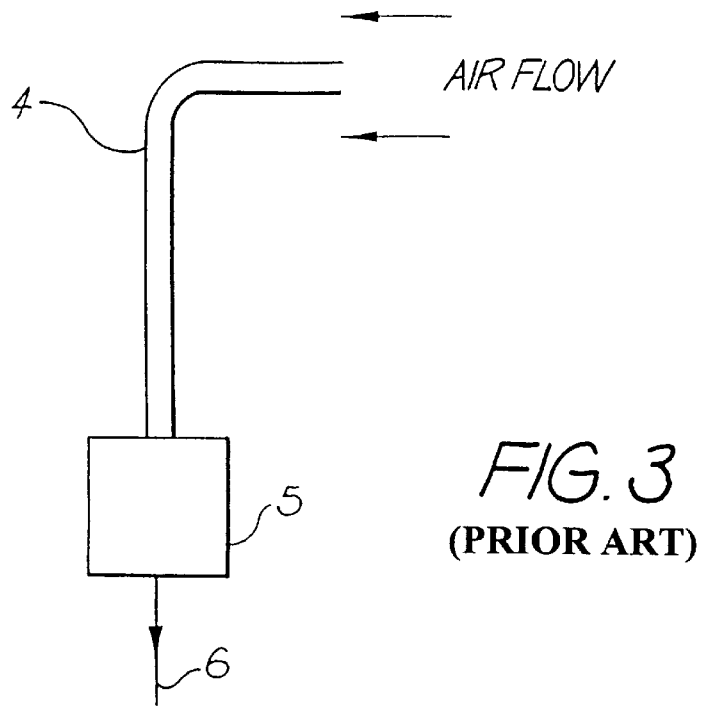
Figure 4:
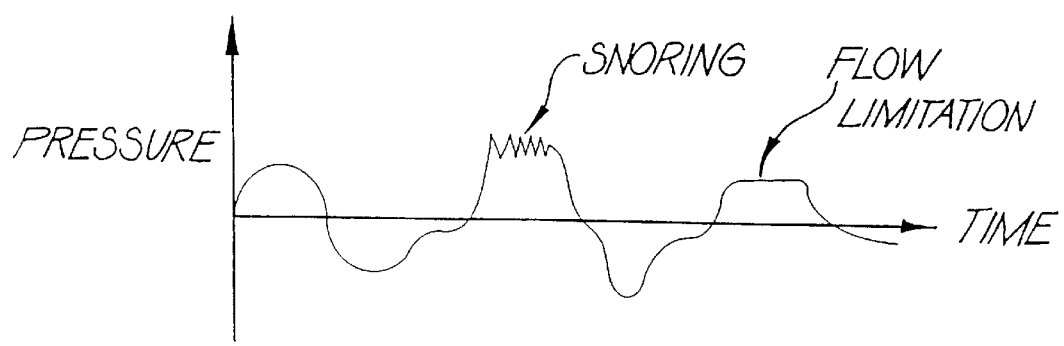
Figure 5:
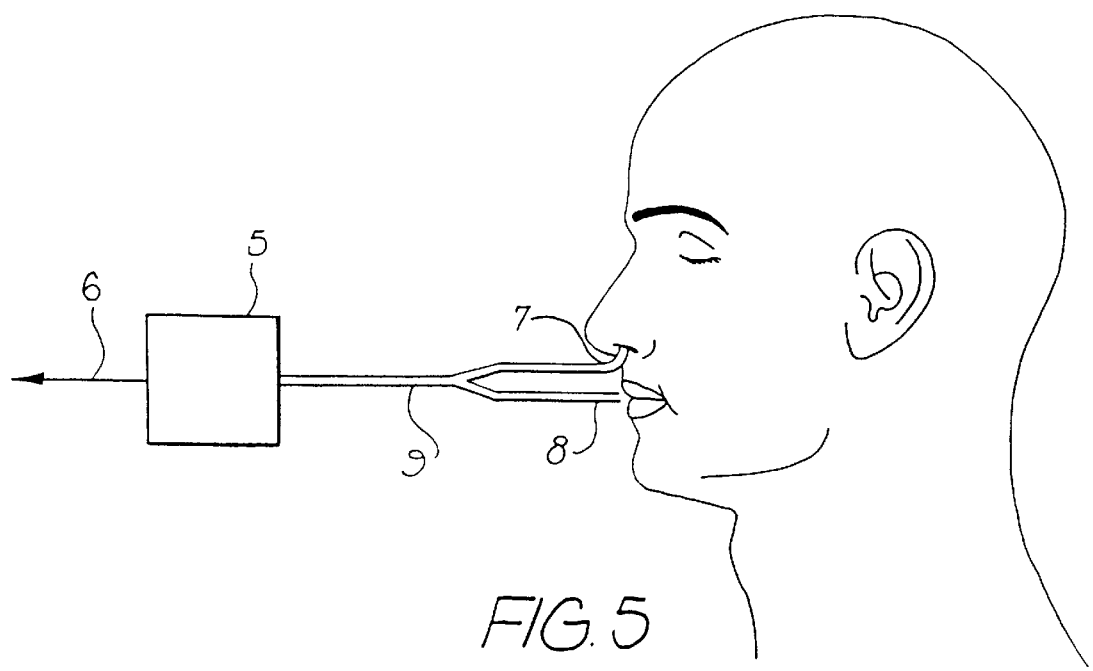
Figure 6:
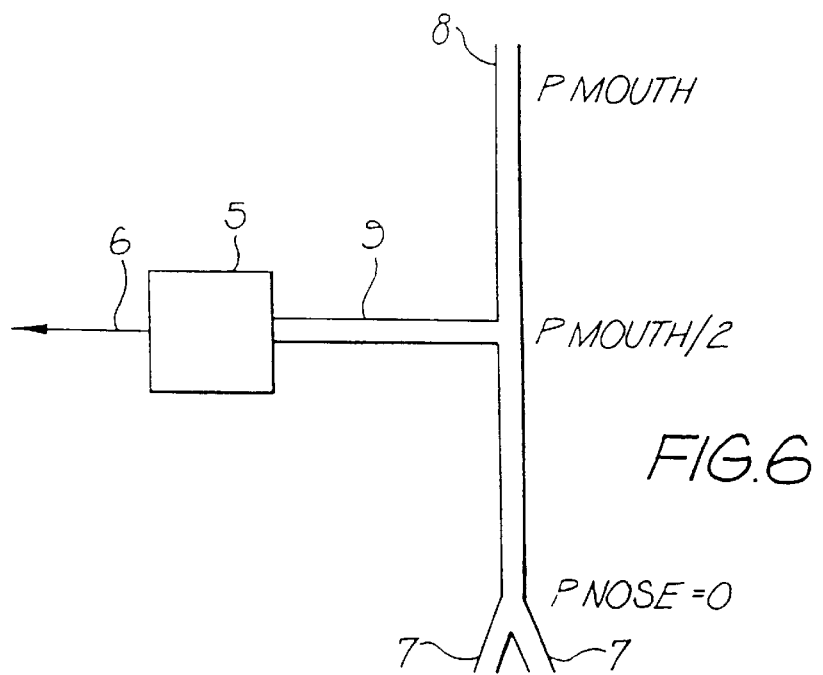
Figure 7A:
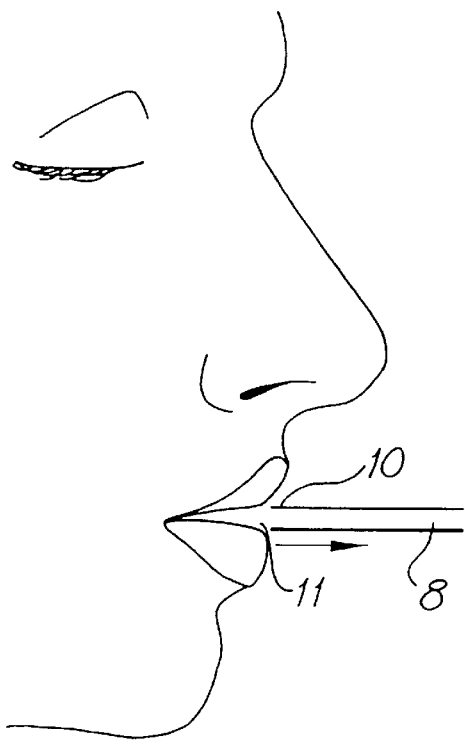
Figure 7B:
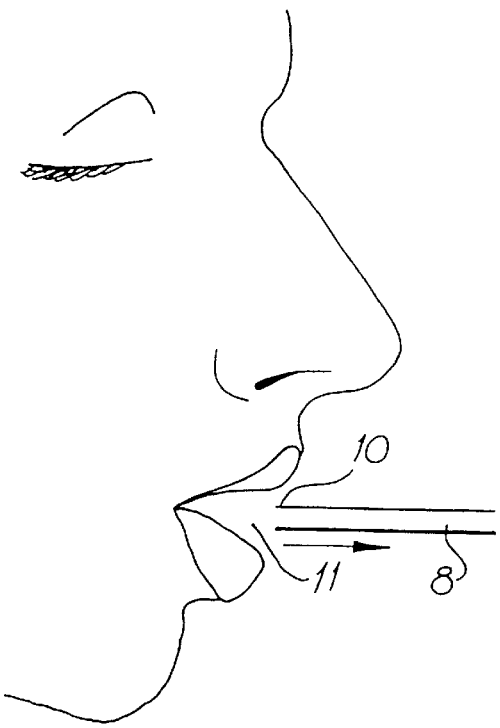
Figure 8A:
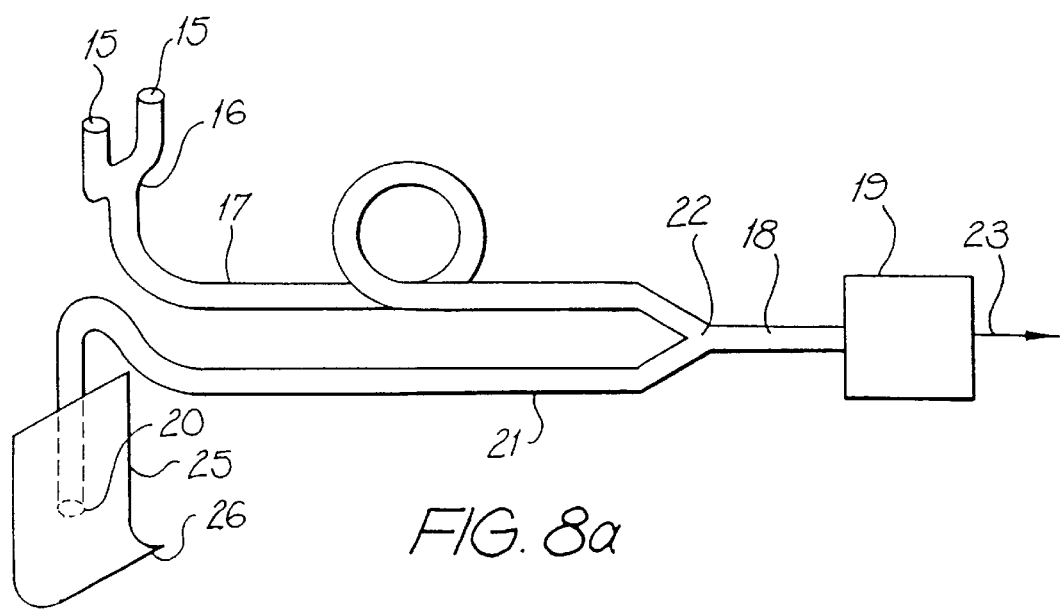
FIGS. 8a and 8b are schematic diagrams of a first embodiment.
Figure 8B:
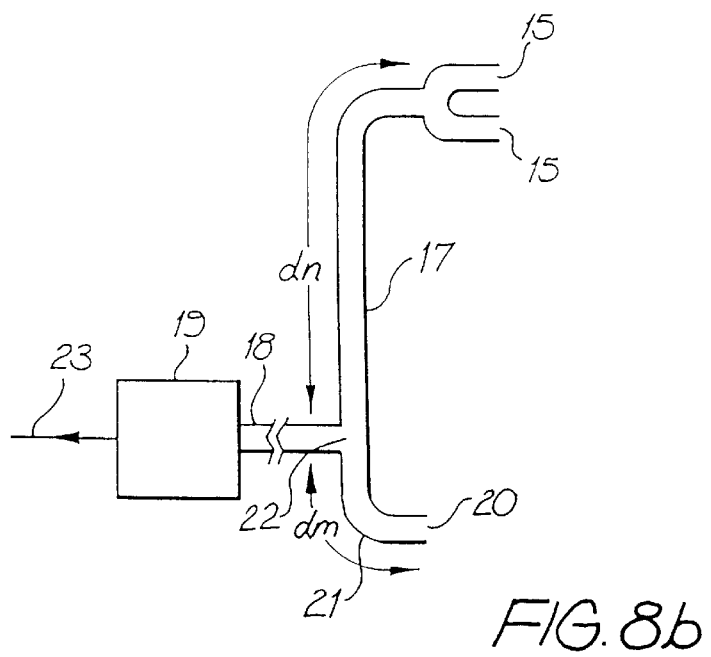
Figure 9:
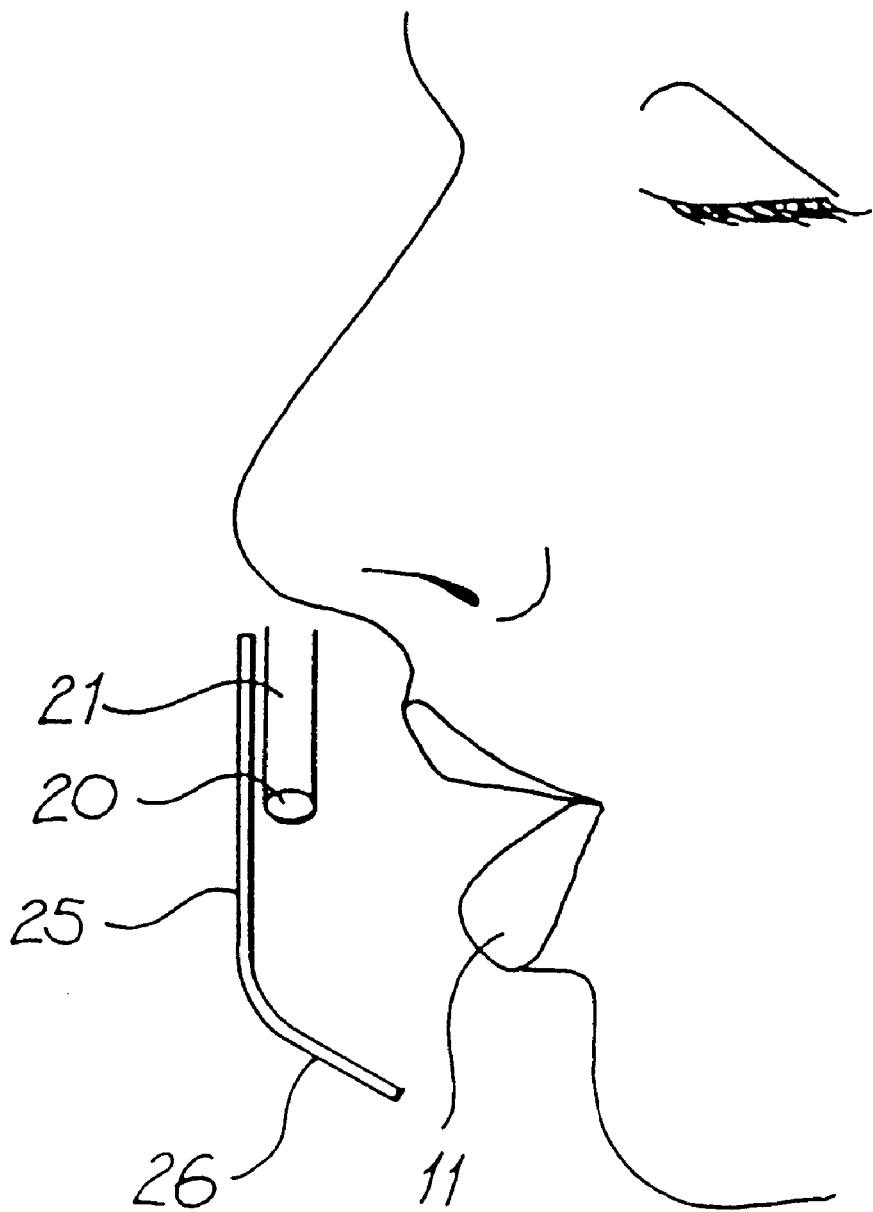
FIG. 9 shows detail of the location of the oral tube end to the mouth.

An embodiment of the invention is shown in FIGS. 8a, 8b and 9, and comprises a pair of nasal prongs, each consisting of a short tube 15 of dimensions suitable for insertion into the lower portion of the nares without unduly blocking the flow of air from the nares to the outside world. The ends of these tubes 15 distal from the patient join together, either directly or via a small plenum chamber 16. After the joint, a single tube 17 continues, conveying the prong (nasal) pressure towards an electrical pressure transducer 19.

Another single (or double) prong is held in proximity with the patient's mouth. The vertical location of the open end 20 of the mouth tube (or tubes) 21 is normally at or below the level of the bottom of the upper lip. The horizontal location of the oral tube (or tubes) 21 may be the saggital midline of the mouth. It can be symmetrically offset from this midline for two tubes. In either case the tube end 20 should locate approximately in the centre of airflow out of a slightly opened mouth.

A baffle element 25 extends downwards from a location above the open end 20 of the oral tube 21 to a level approximately half way between the top of the lower lip and the centre of the labial orifice when the mouth is fully open, as particularly shown in FIG. 9. The baffle element 25 redirects a portion of oral airflow towards the open end 20 of the oral tube 21 and may be curved at its lower extremity 26 to facilitate this function. With the addition of the baffle, the difference in pressure sensor output for constant respiratory flow but different degrees of mouth opening are significantly reduced. The oral tube 21 extends distally from the mouth towards an electrical pressure transducer 14. The oral tube 21 and nasal tube 17 conjoin at a junction 22 to form a common tube 18 connected to the pressure transducer 19.

The diameter of the nasal and oral tubes 17,21 is limited by the impedance of the respective tubes to airflow. The impedance is approximately proportional to the inverse fourth power of the tubing diameter, meaning that very small diameters, no matter how comfortable for a patient, are not suitable for reason of displaying lag and a smoothing-out effects due to the physical transmission difficulties of the air pressure wave in the tube. Testing by the inventors utilising the applicant's Sullivan III CPAP machine with tubing of 1.7 mm inner diameter PVC tubing over a length of 2.56 m produced respiration measurements that included the attributes of snoring and flow limitation. Flow limitation is characterised by high-frequency components that would be the first to be attenuated for too small a tubing diameter. Thus it has been determined that a diameter of 1.7 mm for the tubing performs satisfactorily for normal respiratory flow rates during the administering of CPAP treatment. It is possible that even smaller diameters will perform satisfactorily.

The absolute lengths of the nasal tube 17 and oral tube 21 also have been investigated. An objective is to keep the respective lengths to be at least equal, and approximately 25–30 cm so that the junction 22 can be formed at a point behind the patient's head. Testing was performed for lengths in the range 10 to 50 cm (both tubes being the same length at all times) for nose-only and mouth-only breathing with air flow at an approximately constant value. A normalised ratio of the resultant electrical flow signal for nose breathing to mouth breathing, with respect to a reference flow obtained by breathing through the nose (tube) with the mouth opening 20 blocked, was determined for each length.

| Tube Length (cm) | Normalised ratio |
| --- | --- |
| 50 | 3.5 |
| 40 | 2.4 |
| 30 | 4.7 |
| 20 | 4.8 |
| 10 | 2.5 |
| Mean Value | 3.6 |

From these results it has been determined that any length in the range 10 to 50 cm can be utilised, through 20 to 50 cm lengths are preferred, since this range covers most of physiological values for the half-perimeter of the head. The length of the common tube 18 should be long with respect to the lengths of the nasal and oral tubes 17,21 and typically 150 cm.

This foregoing study made the assumption that the lengths of the nasal tube 17 from the prongs 15 to the junction 22 ($d_n$) is the same as the length of the oral tube 21 from the opening 20 to the junction 22 ($d_m$). Hence it has been determined that the absolute lengths are unimportant to the magnitude of an output pressure signal from either the nasal tube 17 or the oral tube 21, however the ratio of the two needs also to be considered. The ratio $d_n/d_m$ is conveniently termed $\beta$.

The act of breathing genereates an air flow that is either into the respective tube (exhalation) or out of the respective tube (inhalation). Since the pressure transducer 19 is essentially a closed chamber, no continuous flow is possible in the nasal tube 17 or oral tube 21, hence the kinetic energy of flowing air is converted into a pressure wave (potential) according to Bernoulli's equation. This equation can be simplified so that the output signal 23 can be considered as approximately directly proportional to the square of the velocity of the incoming air stream. If the cross-sectional area of the physiological airway is constant, then the linear velocity is constant as well. Under such conditions, the transduced signal 23 will be proportional to the square of the volumetric flow rate.

Proceeding on the assumption that there are air flows, $f_m$ and $f_n$, at each of the mouth and nose, the signal generated at the mouth is $M=k_m f_m^2$ and the signal generated at the nose is $N=k_n f_n^2$, where $k_m$ and $k_n$ are coefficients depending on the area, physical conditions and the pressure transducer used. The total signal, T, as perceived by the pressure transducer 19 is modelled as a weighted arithmetic mean of the signals, with the weights equal to the distances to the other opening 15,20.

$$T = \frac{d_m N + d_n M}{d_m + d_n} \Rightarrow T = \frac{d_m k_n}{d_m + d_n} f_n^2 + \frac{d_n k_m}{d_m + d_n} f_m^2$$

For a single nasal prong 15, and especially for large mouth openings, the signals from the mouth are smaller than those from the nose, e.g. $k_m < k_n$ if the tubing lengths are the same. This is due to the larger mouth area. For the total signal to be meaningful, the lengths of the respective tubing should be adjusted so that for a given flow rate, the signals from mouth-only and nose-only breathing are the same. In order to achieve this result, the ratio of coefficients $k_m$ and $k_n$ must be determined.

The ratio $k_n/k_m$ is termed $\alpha$. To have similar values for the nose and mouth signals, M=N for a given flow rate. The above equation simplifies to be $d_n = d_m \alpha$, hence $d_n/d_m = \beta$, and so $\beta=\alpha$. $\beta$ has been previously determined in relation to the study of the absolute length of the nasal and oral tubes 17,21 to be approximately 3.5. Thus the nasal tube 17 must be approximately 3.5 times further from the junction 22 than the mouth tube 21. This result relates to a "simple" mouth tube. As will be shown, the ratio can be closer to 5:1 in use of the baffle element 25.

When the mouth and nose signals are equal, the nose signal contribution is equal to $1/(\beta+1)$ of its maximum value (if there were no mouth tube), and the mouth signal contribution is equal to $\beta/(\beta+1)$ of its maximum value. Therefore, for $\delta=5$ (say), 5/6 of the nose signal is lost, but only 1/6 of the mouth signal is lost.

The average signal obtained also was considered for a given value of $\delta$. The average can be expressed as:

$$\overline{T}(\alpha, \beta) = \frac{(\beta/\alpha) + 1}{3\beta + 3}$$

For both $\alpha=3.5$ and $\alpha=5$, it was found that beyond the value of $\beta=2$, there are only small additional losses in the average signal, hence the value of $\beta>2$ can be used if convenient without too much additional loss.

A further result of the tests performed is that the signals obtained proved satisfactory by use of only a single pressure transducer, thus leading to the minimizing of costs, volume and the electrical complexity of the monitoring equipment.

The physical location of the nasal cannulae presents no problem in obtaining an accurate assessment of nasal respiratory flow. It is a different situation concerning respiration by the mouth.

Studies were done to determine the appropriate positioning of the end 20 of the oral tube 21 relative to the mouth. Thus measurements were taken for a number of locations of lateral and vertical displacement from the centre of the mouth. In particular, it was found that the measured signal drops markedly when moving upwardly from the centre of a mouth, this presumably being due to shielding of the air flow by the upper teeth. The variation with lateral location was far less sensitive, there being only negligible loss of signal amplitude for points midway between the centre of the mouth and the edges of the mouth. The effect of angle from the flow centreline also was investigated, and it was determined that even up to a 45° deviation from the flow centreline still obtained a 75% retention of the flow signal.

Another requirement that resulted from the flow measurement testing was that the oral tube 21 in the vicinity of the opening 20 must be kept particularly stable in order to obtain good reproducability. Further investigation indicated that the deflector arrangement previously described gave satisfactory results in that it re-directs flow so that it always enters the nasal tubing opening 20 with the same orientation.

The planar arrangement for the baffle 25 shown in FIGS. 8 and 9 was preferred to an arrangement such as a three-sided single open-ended box. The dimensions of the baffle 25 also were considered. Tests were conducted for a variable width of the baffle 25 commencing with the width of 7 cm down to 1 cm. Signal amplitude remained essentially constant down to 3 cm width decreasing to approximately 95% of its value at 7 cm in going to a width of only 1 cm. In order to maintain the baffle 25 as having sufficient rigidity, it has been determined that a minimum width of 2 cm is required. The length of the baffle also was considered. A length of 4 cm was estimated to be the maximum height of the mouth opening, and hence this distance was the limit for the "active height" of the baffle for physiological breathing. The "active height" is defined as the height over which the air flow is deflected before entering the opening 20 of the oral tube 21. Clearly the deflector has to be longer than its active height to allow for attachment to a background plate of the mask supporting the deflector.

So far as location of the opening 20 of the oral tube 21 is concerned, various positionings were investigated, and it was found that the optimal signal is obtained for the opening positioned at, or up to 1.2 cm above, the flow centreline. For a value of 2 cm above the centreline, more than 62% signal retention was obtained, however it became apparent that if the opening is located below the level of the upper teeth, exhalation can produce negative resultant signals. This thought to be due to some form of entrainment. As a result, it was determined to locate the opening 20 in a position as close as possible to the flow centreline and protruding 0.5 cm below the upper lip. The sensitivity to small changes in position of the nasal tube 21 for various mouth openings was found to be small. It was also determined, however, that the ratio of nasal tubing and oral tubing lengths should be closer to 5:1 for the case of use of the deflector baffle 25. This ratio represents the ratio of the impendances to flow of the two tubings 17,21 that allows the mouth and nose to give similar contributions to the transduced signals.

Whilst it is possible to adjust the relative impedances of the nasal tubing and oral tubing to give the desired 5:1 ratio, it is equally possible to vary the diameter of the respective tubes whilst retaining them at equal lengths. Since impedance is approximately a function of the inverse fourth power, the diameter of the nasal tube 17 need only be reduced by a factor of $5^{1/4}$=1.5.

It is equally possible to obtain the required impedance ratios by combination of adjustments of the lengths and diameters in accordance with the empirical techniques described above.

Figure 10A:
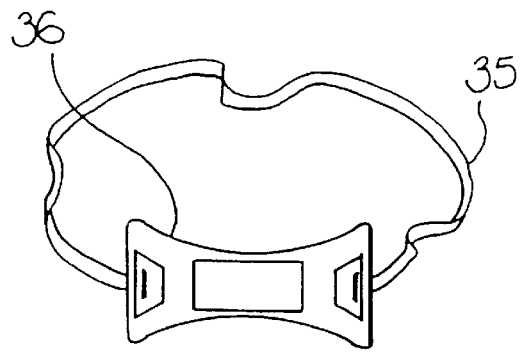
FIGS. 10a–d show an embodiment of a mask to be worn by a patient that monitors oral and nasal respiration.
Figure 10B:
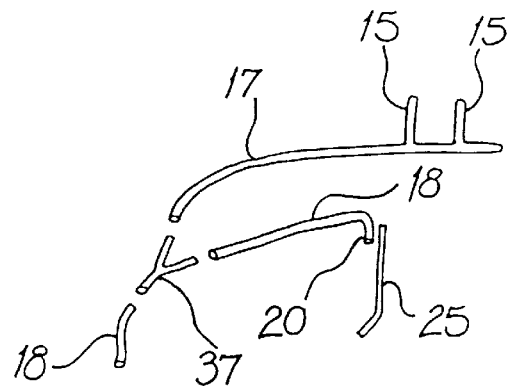

FIGS. 10a–d show an arrangement for the monitoring of oro-nasal respiration, in the form of a mask that is fastened to the head by means of a resilient strap fitting around the head of a patient. The strap 35 is secured to the opposed ends of a trapezoidal base plate (or mask body) 36. The mask body 36 typically is of silicone material, 2 cm thick, 6 cm in length and 2.5 cm in height at the ends. The height at the middle of the body 36 typically is 0.5 cm. The tubing attached to the mask is shown in FIG. 10b, together with the deflector plate 25 associated with the mouth prong 20. The nasal prongs 15 are approximately 2 cm long with a 1.5 cm spacing between them. The nasal tube 17 conjoins the oral tube 18 at the nylon Y joint 37, in turn coupled to the common tube 18 the nasal tube 17 has a typical length of 140 cm, the nasal tube being of length 45 cm.

Figure 10C:
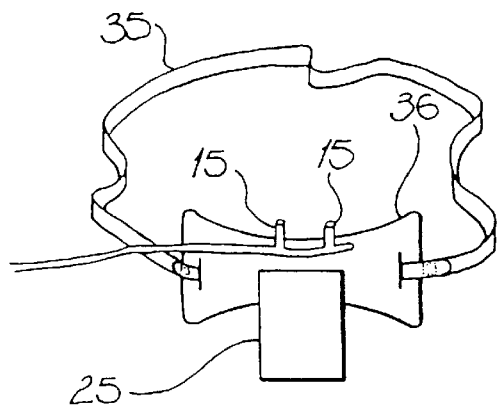
Figure 10D:
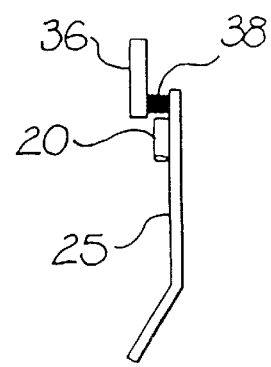

FIG. 10c shows the mask body 36 with the nasal prong 15 in place and the relative location of the deflector plate 25. The deflector plate has a typical length of 4 cm and width of 2 cm. As shown in FIG. 10d, the deflector plate 25 is mounted off the mask body 36 by a sustaining ellipsoid 38. Only a portion of the mouth prong 20 is shown, relevantly having a typical length of 1 cm in the plane of the deflector 25.

The electrical signal 23 output from the transducer 19 is representative of respiratory flow, whether that be by the nose, the mouth or the nose and mouth in combination, must be processed to obtain meaningful information concerning the respiratory phenomena of respiratory "swings" and snoring. The swings are characterised by low frequency, high amplitude pressure variations, while snore is characterised by yet higher frequency, but lower amplitude pressure variations. The nature of these characteristics is antagonistic to amplifier and discrimination circuitry. The ability to determine instances of respiratory swing and snoring can provide the physician with greater diagnostic powers than by conventional oscillogram recordings.

Figure 11:
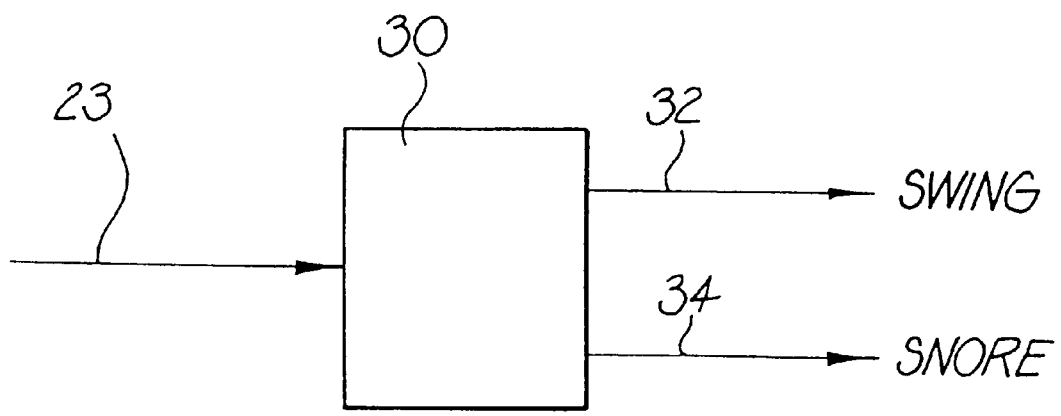
FIGS. 11 and 12 show schematic circuit diagrams of a signal processing circuit.

FIG. 11 shows a general schematic diagram of a signal processing circuit 30 to which the signal 23 from the pressure transducer 19 is input. Two output signals are derived, being a swing signal 32 and a snore signal 34. The SWING output signal 32 is a trace of the cyclic zero-crossing swing of respiratory flow. The SNORE output signal 34 also is a continuous trace that not only indicates the occurrence of snoring, but also can be calibrated to give a measure of snoring, possibly in decibels.

Figure 12:
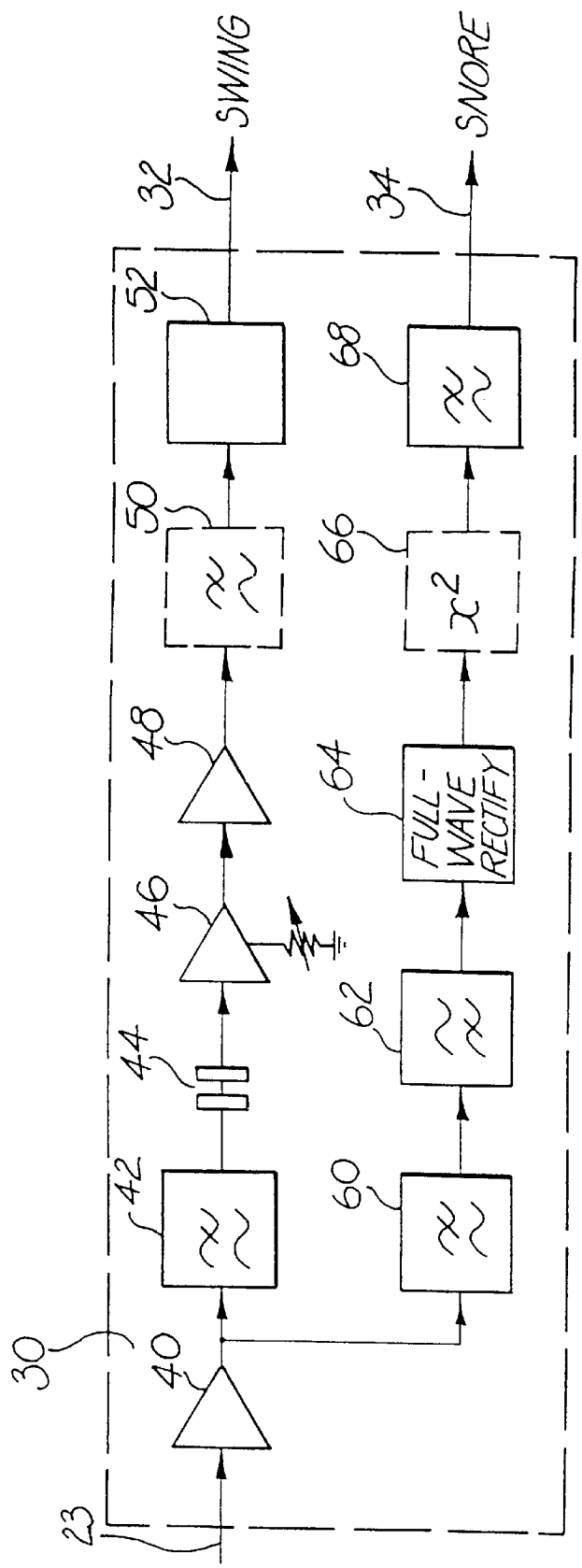

FIG. 12 shows a schematic circuit diagram of the signal processing circuit 30. The signal 32 from the pressure transducer is a direct measure of respiratory flow achieved by the Bernoulli effect. The signal is input to a buffering amplifier 40 that can be differential in nature in the event that a two-wire pressure transducer is used. In the alternative, an internal reference voltage could be provided to such a differential amplifier stage 40 to provide an appropriate offset adjustment. The output from the amplifier 40 splits into two signal parts relative to a determination of SWING and a determination of SNORE. In the SWING signal path, the signal passes to a low-pass filter 42, typically with a 5 Hz cut-off, to reduce noise such as that due to snoring. The output of the filter 42 is AC coupled by means of a capacitor 44 to a variable gain amplifier stage 46. There then follows a further amplification stage 48 in the nature of either a two-level automatic gain controlled amplifier or a non-linear amplifier (typically square-law). The effect of the amplification stage 48 is to boost low level signals in amplitude relative to a high level signals, particularly since signals obtained from mouth breathing only can vary appreciably in consequence of the cross-sectional area of the mouth opening. The output from the amplification stage 48 passes to an optional low pass filter 50 providing noise reduction, and to a scaler/level shifting stage 52 that provides appropriate adjustment of the signal level so that the SWING signal 32 can be applied to further processing stages, and typically to an analog-to-digital converter having a voltage range of 0–5 volts, in turn being suitable for application to a microprocessor device.

In the SNORE path, the signal output from the amplifier 40 passes to a low-pass filter 60 in turn to a high-pass filter 62, in the combination forming a band-pass filter. The band-pass frequency range typically will be 20–300 Hz, this representing the frequencies characterised by snoring. The output signal from the high-pass filter 62 is full-wave rectified by a rectifying stage 64. The rectified form of the band-passed flow signal is a first-order approximation of the power of the signal. If a better approximation is required, the rectified signal can then be squared in a squaring stage 66 drawn as being optional. The signal then is low-pass filtered to remove harmonic components and noise in the filter stage 68, resulting in the output SNORE signal 34.

What is claimed is:

1. An apparatus for monitoring oro-nasal respiration comprising a nasal tube for receiving nasal respiratory flow and an oral tube for receiving oral respiratory flow, the pneumatic impedances of the nasal tube and the oral tube being arranged to be different so that the contributions of respiratory airflow from each of said tubes are substantially equal, and electrical transducer means to which both said oral tube and said nasal tube are coupled for generating an output signal representative of oro-nasal respiration.

2. Apparatus for detecting oro-nasal respiratory flow, comprising a nasal tube for receiving nasal respiratory flow and an oral tube for receiving oral respiratory flow, the pneumatic impedances of the nasal tube and the oral tube being arranged to be different so that the contributions of respiratory airflow from each said tube are substantially equal.

3. The apparatus as claimed in claim 2, wherein the respective said pneumatic impedances are in a ratio substantially the same as the ratio of amplitudes of nasal respiratory flow and oral respiratory flow.

4. The apparatus as claimed in claim 2, wherein said nasal tube terminates in a pair of nasal prongs, and said oral tube is open ended.

5. The apparatus as claimed in claim 3, wherein the nasal tube is of longer length than the oral tube to effect said different pneumatic impedances.

6. The apparatus as claimed in claim 5, wherein the ratio of the nasal tube length to the oral tube length is less than about 5:1.

7. The apparatus as claimed in claim 6, wherein the nasal tube is of longer length than the oral tube and the relative diameter of the nasal tube is smaller than the diameter of the oral tube to effect said different pneumatic impedances.

8. The apparatus as claimed in claim 6, wherein the diameter of the nasal tube is smaller than the diameter of the oral tube to effect said different pneumatic impedances.

9. The apparatus as claimed in claim 8, wherein the ratio of the nasal tube diameter to the oral tube diameter is about 2:3.

10. The apparatus as claimed in claim 1, wherein the respective said pneumatic impedances are in a ratio substantially the same as the ratio of amplitudes of nasal respiratory flow and oral respiratory flow.

11. The apparatus as claimed in claim 10, wherein the nasal tube is of longer length than the oral tube to effect said different pneumatic impedances.

12. The apparatus as claimed in claim 10, wherein the nasal tube is of longer length than the oral tube and the relative diameter of the nasal tube is smaller than the diameter of the oral tube to effect said different pneumatic impedances.

13. The apparatus as claimed in claim 11, wherein the ratio of the nasal tube length to the oral tube length is less than about 5:1.

14. The apparatus as claimed in claim 13, wherein the diameter of the nasal tube is smaller than the diameter of the oral tube to effect said different pneumatic impedances.

15. The apparatus as claimed in claim 14, wherein the ratio of the nasal tube diameter to the oral tube diameter is about 2:3.

16. The apparatus as claimed in claim 1, wherein said nasal tube terminates in a pair of nasal prongs, and said oral tube is open ended.

17. The apparatus as claimed in claim 16, wherein said nasal tube and said oral tube conjoin at an end opposite to said nasal prongs and said open end respectively to form a common tube, the common tube in turn being coupled to said electrical transducer means.

18. The apparatus as claimed in claim 16, wherein said nasal tube and said oral tube conjoin at an end opposite to said nasal prongs and said open end respectively to form a common tube, the common tube in turn being coupled to said electrical transducer means.

19. The apparatus as claimed in claim 17, further compromising a mask body carrying said nasal prongs adapted to be worn by a patient, and from which depends a baffle arrangement that, when said mask body is being worn, is proximate the patient's mouth, and wherein a portion of said oral tube is mounted from said baffle in a manner such that said open end is interposed between the baffle and the patient's mouth.

20. The apparatus as claimed in claim 17, further compromising a mask body carrying said nasal prongs adapted to be worn by a patient, and from which depends a baffle arrangement that, when said mask body is being worn, is proximate the patient's mouth, and wherein a portion of said oral tube is mounted from said baffle in a manner such that said open end is interposed between the baffle and the patient's mouth.

21. The apparatus as claimed in claim 19, wherein said baffle is of curved shaped to direct oral respiration to said open end of said oral tube.

22. The apparatus as claimed in claim 19, wherein said baffle is of curved shaped to direct oral respiration to said open end of said oral tube.

23. The apparatus as claimed in claim 21, wherein said baffle is of dimensions that result in coverage of the full open extent of the patient's mouth.

24. The apparatus as claimed in claim 21, wherein said baffle is of dimensions that result in coverage of the full open extent of the patient's mouth.

25. The apparatus as claimed in claim 1, wherein said electrical transducer means, in use, produces an output electrical signal that is representative of respiratory flow.

26. The apparatus as claimed in claim 25, further comprising an electrical circuit that receives said respiratory flow signal, and including a first filtering sub-circuit that generates an output signal indicative of cyclic zero-crossing swing of respiration.

27. The apparatus as claimed in claim 25, further comprising an electrical circuit that receives said respiratory flow signal, and including a first filtering sub-circuit that generates an output signal indicative of cyclic zero-crossing swing of respiration.

28. The apparatus as claimed in claim 26, wherein said electrical circuit further includes a second filtering sub-circuit that generates an output signal indicative of the occurrence of a patient snoring.

29. The apparatus as claimed in claim 26, wherein said electrical circuit further includes a second filtering sub-circuit that generates an output signal indicative of the occurrence of a patient snoring.

30. The apparatus as claimed in claim 28, wherein said first filtering sub-circuit comprises the cascade connection of a low pass filter, ac coupler and a 2-level non-linear amplifier, and said first filtering sub-circuit comprises a band pass filter and a full wave rectifier.

31. The apparatus as claimed in claim 28, wherein said first filtering sub-circuit comprises the cascade connection of a low pass filter, ac coupler and a 2-level non-linear amplifier, and said first filtering sub-circuit comprises a band pass filter and a full wave rectifier.

32. The apparatus as claimed in claim 1, wherein said electrical transducer means, in use, produces an output electrical signal that is representative of respiratory flow.

33. A method for monitoring oro-nasal respiration comprising the steps of locating a nasal tube in the vicinity of a patient's nares to receive nasal respiratory flow, locating a mouth tube in the vicinity of the patient's mouth to receive oral respiratory flow, arranging the pneumatic impedances of the nasal tube and the oral tube to be different so that the contributions of respiratory airflow from each said tube are substantially equal, and converting, by electrical transducer means, flow in said oral tube and said nasal tube to a signal representative of oro-nasal respiration.

34. The method of claim 33, comprising the further step of:

selecting the respective said pneumatic impedances to be in a ratio substantially the same as the ratio of amplitudes of nasal respiratory flow and oral respiratory flow.

35. The method of claim 34, comprising the further step of:

filtering said oro-nasal respiration signal to generate an output signal indicative of a cyclic zero-crossing swing of respiration.

36. The method of claim 35, comprising the further step of:

processing said oro-nasal respiration signal to generate an output signal indicative of the occurrence of snoring.

* * * * *